United States Patent [19]

Stein et al.

[11] 3,949,615

[45] Apr. 13, 1976

[54] ANALYSIS APPARATUS

[75] Inventors: Bernard Stein, Andover; Gustav H. Dreier, Acton, both of Mass.

[73] Assignee: Instrumentation Laboratory, Inc., Lexington, Mass.

[22] Filed: May 13, 1974

[21] Appl. No.: 469,080

[52] U.S. Cl. ............................................. 73/423 A
[51] Int. Cl.² ............................................. G01N 1/14
[58] Field of Search ......... 73/42 BR, 423; 222/129, 222/204, 156, 424.5, 437, 457, 485, 576; 137/261, 453; 204/195 B

[56] References Cited
UNITED STATES PATENTS

| | | | |
|---|---|---|---|
| 1,235,316 | 7/1917 | Henderson | 137/453 |
| 3,252,330 | 5/1966 | Kling | 73/423 A |
| 3,546,946 | 12/1970 | Smith | 73/423 A |

FOREIGN PATENTS OR APPLICATIONS

| | | | |
|---|---|---|---|
| 821,686 | 11/1951 | Germany | 137/453 |

*Primary Examiner*—S. Clement Swisher

[57] ABSTRACT

A flush system for electrochemical analysis apparatus comprising a reservoir of flush solution, a flush chamber connected thereto and open at the top, and a sample entrance (probe) arranged for movement between an immersed position in the flush chamber and a sampling position removed from the flush chamber.

24 Claims, 7 Drawing Figures

ANALYSIS APPARATUS

SUMMARY OF INVENTION

This invention relates to apparatus for the analysis of liquid sample constituents, such as constituents of blood. More particularly this invention relates to a system for cleaning such apparatus between the introduction of separate liquid samples into the apparatus. It is necessary to thoroughly clean the sample flow path along which successive samples are drawn, including both interior and exterior surfaces of the sample entrance to remove the residue from one sample which might contaminate successive samples.

It is an object of this invention to provide novel and improved apparatus for cleaning an analysis system of the type in which separate liquid samples are successively introduced into the system.

Another object of the invention is to provide novel and improved analysis system cleaning apparatus which operates with simple mechanical movement and with relatively simple fluid control.

Another object of this invention is to provide an improved flush system in which a sample entrance is moved between two positions, one in a flush chamber and the other out of said chamber, the chamber in communication with a flush reservoir.

In general this invention features cleaning apparatus for an analysis system of the type that has a sample passage having an entrance, a sensor in communication with the passage and a pump for moving a sample through the passage, a reservoir for cleaning liquid, a flush chamber open at the top and communicating with the reservoir, and means for moving and guiding the sample entrance between a cleaning position in the flush chamber and a sampling position removed therefrom.

Preferred embodiments include the feature that communication of the flush chamber and the reservoir is through a restricted opening whereby the pump may be operated to remove cleaning liquid from the chamber more rapidly than it may be replenished through said opening thereby entraining air in the cleaning liquid for scrubbing action flow through the sample passage after an initial continuous flow of solution. Other features include the provision of an intermediate chamber arrangement for controlling liquid level in the flush chamber; a liquid level indicator chamber communicating with the intermediate chamber; and syphon means connecting the reservoir and then intermediate chamber.

A particular embodiment also includes a guideway above the flush chamber, a holder supported in the guideway for movement toward and away from the flush chamber, the sample entrance being carried by the holder for movement therewith, a biasing member connected to the holder urging the sample entrance toward the flush chamber and a latch engageable with the holder for releasably maintaining the sample entrance in a position spaced from the flush chamber. In that particular embodiment a sensor is provided for detecting and signalling the position of the holder.

Thus preferred embodiments of the invention provide an initial continuous liquid flow of flush solution followed by a flow of liquid with entrained air; an automatic syphon feed of flush solution to the flush chamber; convenient reservoir supply viewing means; convenient moving and guiding means for positioning the sample entrance alternately in sample position and cleaning position; means for automatically returning the sample entrance to the cleaning position in response to an electrical signal; and an electrical interlock responsive to the placing of the sample entrance in the cleaning position.

Other objects, features and advantages of this invention will be apparent to those skilled in the art from the following detailed description of a particular embodiment thereof taken together with the accompanying drawings, in which.

Figure 4:
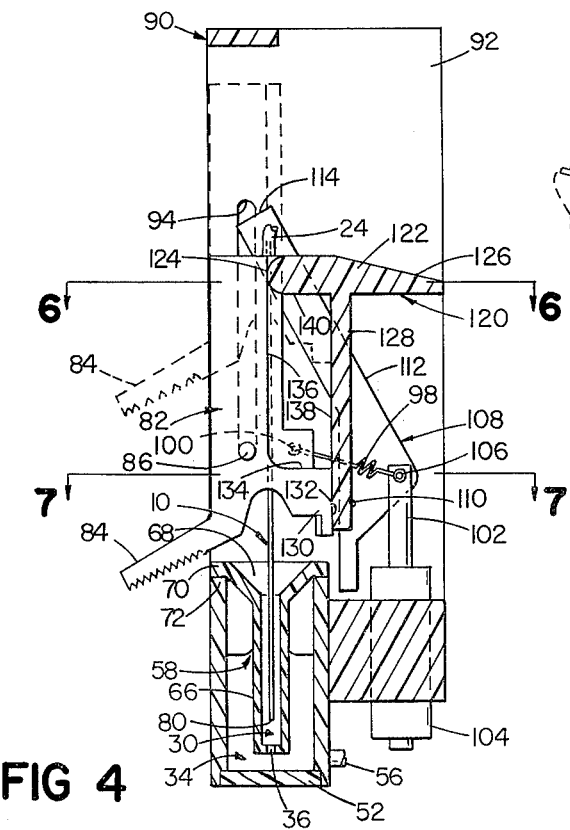
FIG. 4 is a sectional view taken along the line 4—4 of FIG. 2 showing the sample probe in a flush position.
Figure 5:
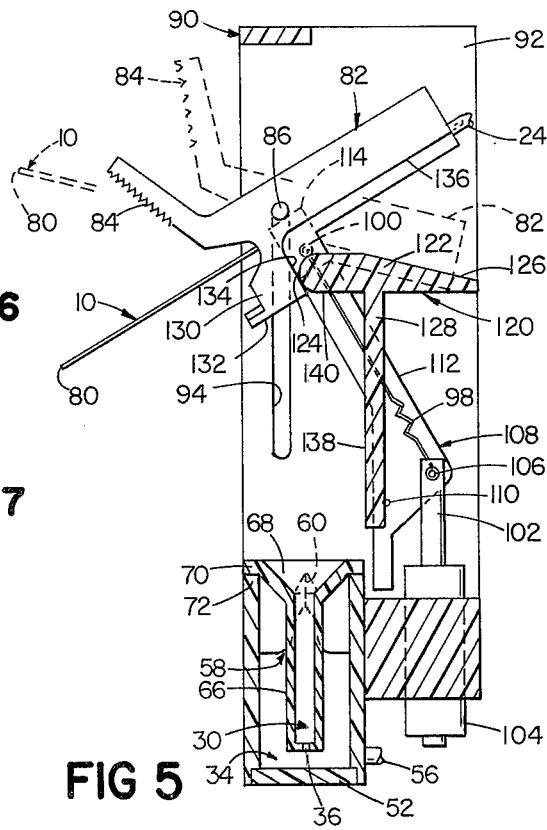
Figure 6:
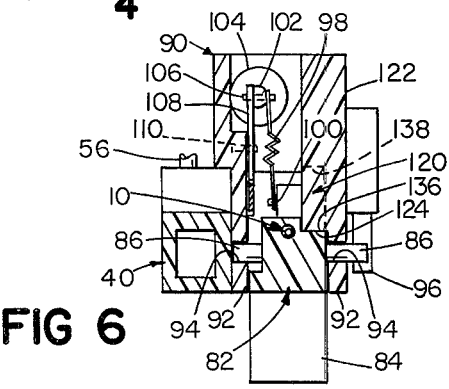
Figure 7:
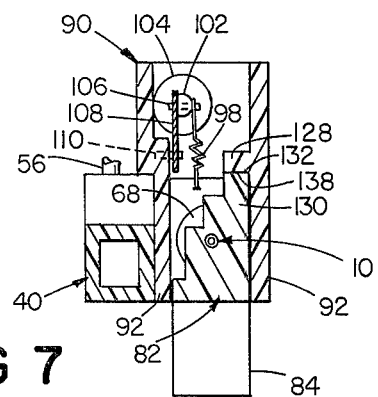

FIG. 5 is a sectional view similar to that of FIG. 4 showing the sample probe in a sampling position; and FIGS. 6 and 7 are sectional views taken along the lines 6—6 and 7—7 of FIG. 4.

DESCRIPTION OF PARTICULAR EMBODIMENT

Figure 1:
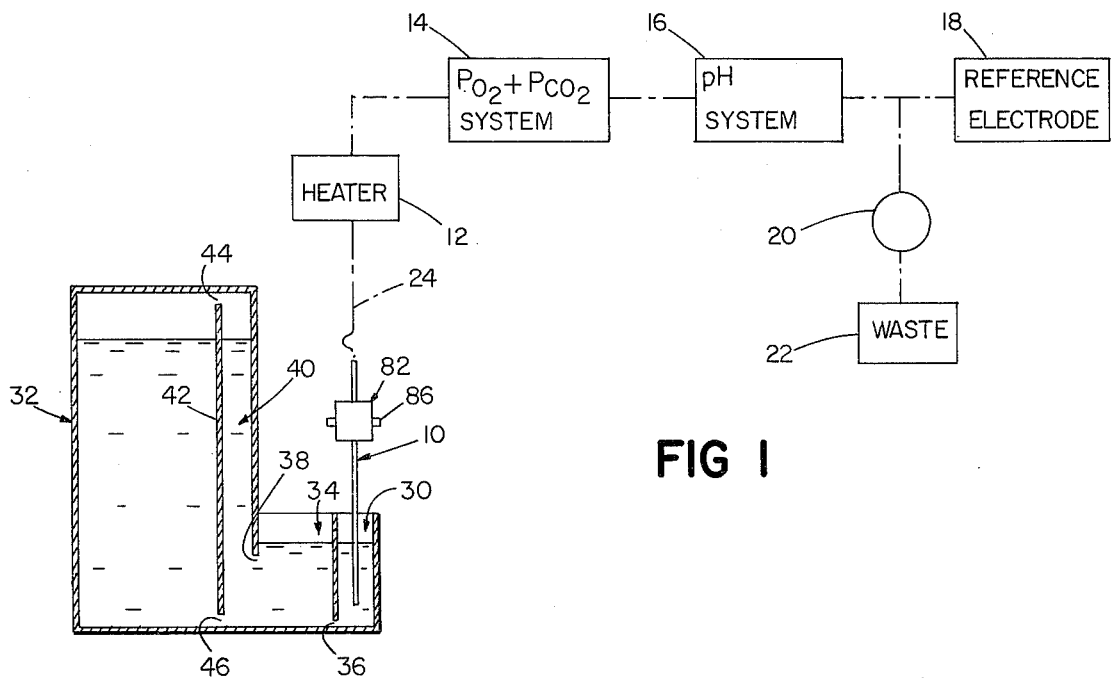
FIG. 1 is a diagrammatic representation of portions of an electrochemical analysis system embodying the invention.

With reference to the drawings and particularly FIG. 1 thereof, an electrochemical analysis system comprises an elongated sample probe 10 through which a sample may be drawn into an analysis chamber. Connected in series with probe 10 are a heater 12 for standardizing sample temperatures, a first sample chamber 14 into which extend electrodes for measuring $PO_2$ and $PCO_2$ (partial pressure of oxygen and carbon dioxide) in a sample, a second sample chamber 16 having an electrode for measuring pH (hydrogen ion concentration) in the sample, a reference electrode 18 connected to the sample passage, a pump 20 for moving fluid through the apparatus and a waste container 22 for receiving liquids pumped through the apparatus. Flexible plastic tubing 24 is used in part for passage of fluids through the apparatus. Pump 20 is preferably a positive displacement peristaltic pump. One or more branch lines (not shown) may be connected to tubing by suitable valving for introducing calibrating fluids into the apparatus.

Figure 2:
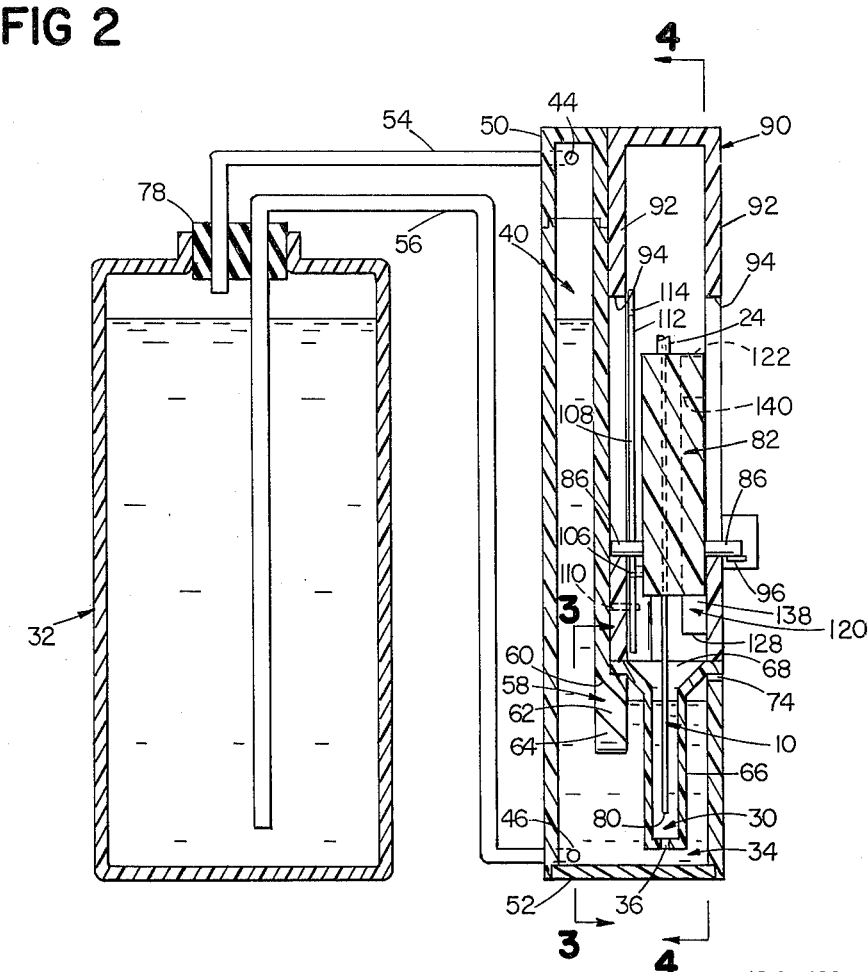
FIG. 2 is an enlarged vertical sectional view of the portion of a particular embodiment of apparatus that is functionally similar to that shown in FIG. 1.

Flush solution storage and feeding apparatus, shown diagrammatically in FIG. 1 and in a particular embodiment in FIG. 2, is positioned adjacent probe 10. In this embodiment, which is used for blood analysis, probe 10 is a stainless steel tube that has an inner diameter of 0.02 inch. The flush apparatus comprises a flush chamber 30 into which probe 10 may be inserted and a flush solution reservoir 32. Disposed between chamber 30 and reservoir 32 is an intermediate chamber 34 that communicates with chamber 30 through restricted orifice 36 and that communicates with reservoir 32 through port 38. An indicator chamber 40 is defined by barrier 42 which has openings or ports 44, 46 at its upper and lower ends, respectively.

In the embodiment shown in FIG. 2, indicator chamber 40 is a tubular, vertically positioned member and is closed on its top by fitting 50 and on its bottom by plate 52, each cemented in position for fluid tight joints. Fitting 50 includes vent opening 44 which is connected to reservoir 30 by tubing 54.

Figure 3:
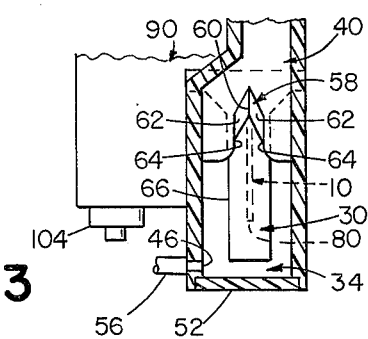
FIG. 3 is a fragmentary view taken along the line 3—3 of FIG. 2.

Intermediate chamber 34 is formed integrally with indicator chamber 40 and is open on the top, closed on its sides, and in the particular embodiment of FIG. 2, is closed on its bottom by plate 52 cemented in position. Its height is a minor fraction of the height of indicator chamber 40. Flush solution feed opening 46 is located at the base of indicator chamber 40 and is connected to reservoir 32 by tube 56. Opening 38 is defined in part by notch 58 that has an inclined peak 60, sloped upper side walls 62 and vertical lower side walls 64 (FIG. 3).

Flush chamber 30 in the embodiment shown in FIG. 2 is a removable member of acrylic plastic that has a tubular lower section 66 about one inch in length and about one-fourth inch in diameter, and a funnel shaped upper end 68 with a surrounding lip 70 removably resting on ledge surfaces 72 of intermediate chamber 34. Port 74 adjacent the upper edge of intermediate chamber 34 provides communication of atmospheric pressure to the interior of intermediate chamber 34 with flush chamber 30 in position. The lower end 76 of flush chamber 30 is spaced above and adjacent the bottom of intermediate chamber 34. Restricted opening 36 (0.015 inch in diameter) in the bottom of flush chamber 30 communicates the interior of flush chamber 30 with intermediate chamber 34.

Reservoir 32 in the embodiment shown in FIG. 2 comprises a plastic bottle with a plug 78 closing its top opening. The bottom of reservoir 32 is aligned with the bottoms of the indicator and intermediate chambers 40, 34. The upper end of reservoir 32 is at approximately the same height as that of indicator chamber 40. A flexible plastic vent tube 54 is connected between vent opening 44 of indicator chamber 40 and the interior upper end of reservoir 32. A flexible plastic syphon tube 56 is connected between feed opening 46 of intermediate chamber 34 and the interior lower end of reservoir 32.

As best shown in FIGS. 4 and 5, probe 10 is mounted for movement between two positions, one with the sample entrance 80 thereof in a lowered vertical flush position extending downwardly into the lower section 66 of flush chamber 30, as shown in FIG. 4, and the other in a raised angularly disposed sampling position for receiving test samples, as shown in FIG. 5. In its lowered position the end 80 of probe 10 is spaced above and adjacent the restricted opening 36 of flush chamber 30. Notch opening 58 between indicator chamber 40 and intermediate chamber 34 has its peak 60 spaced substantially above the lower end 80 of probe 10 in its lowered position as indicated in FIG. 3.

Probe mounting and positioning structure guides and maintain probe 10 in its raised and lowered positions. Probe 10 comprises a tube having a central passage therethrough defining at its lower end a sample entrance 80. At its upper end, probe 10 is connected to plastic tube 24. Probe 10 is, medially of its length, press fitted through a probe holder 82. On its front side, probe holder 72 has a generally horizontally forwardly extending handle 84 for manual positioning thereof. Guide pins 86 project horizontally from either side of holder 82.

The probe guide structure 90 includes vertically extending side walls 92 on each side of probe holder 82, as shown in FIG. 2. Vertically aligned guide slots 94 are formed in walls 92 and slidably receive the ends of guide pins 86. The upper and lower ends of slots 94 define the upper and lower limits of movement of holder 82 in the raised and lowered positions of probe 10, the upper ends of the slots 94 being spaced above the lower ends thereof a distance greater than the distance between the lower end 80 of probe 10 and the upper end of cup 30 in the lowered position of probe 10. One pin 86 extends beyond one of the walls 92 through slot 94 to engage a microswitch 96 (FIG. 2) that provides an indication of probe position.

A tension spring 98 (FIGS. 4 and 5) is connected to pin 100 carried by probe holder 82 at a position spaced generally horizontally rearwardly of pin 86, with the holder 82 in its lowered position (FIG. 4). The other end of spring 98 is connected to arm 102 of vertically positioned solenoid 104 by pin 106 located generally horizontally rearwardly of pin 100 in the lowered position of holder 82.

A latch member 108 is also connected to solenoid arm 102 by pin 106 and is pivotally connected to guide structure 90 by pin 110. Latch member 108 has an arm 112 that extends to the upper end of guide slots 94 and defines a latch surface 114 which engages a pin 86 to secure probe 10 in its raised or sampling position, as shown in FIG. 5.

A guide projection 120 formed in the outer wall 92 includes a horizontal web 122 with a curved leading edge 124 and an inclined rearwardly extending upper surface 126; and a vertical web 128. Holder 82 includes a vertically extending rear surface 136 and a rearwardly extending projection 130 that has a rear surface 132 biased into engagement with surface 138 of web 128 by spring 98 in the position shown in FIG. 4 and an upper surface 134. In the lowered position (FIG. 4), projection surface 132 is in engagement with web surface 138 and holder surface 136 is in engagement with the curved surface 124 of horizontal web 122.

As handle 84 of holder 82 is manually lifted to move probe 10 into its raised position as shown in FIG. 5 from its lowered position as shown in FIG. 4, surface 136 slides upwardly along surface 124 and rear surface 132 of projection 130, which is biased against vertical web 128 by spring 98, slides upwardly along web 128, the vertical movement of holder 82 being guided by pins 86 in grooves 94. Vertical holder guide surface 136 slides along curved surface 124 and opposes the tendency of holder 82 to rotate in the clockwise direction as viewed in FIG. 4. When the junction of surfaces 134 and 136 is reached, further upward movement of holder 82 is impeded by horizontal web 122 but that horizontal web allows rotation of the holder 82 toward the position shown in FIG. 5. As the holder is raised, spring 98 is tensioned, increasing the force urging the latch 108 in the counterclockwise direction. As pins 86 move to the upper end of slots 94, one pin cams past the latch and as soon as the pin has moved past the latch, that latch moves forward into the latching position shown in FIG. 5 and secures the holder in elevated position. In this position the tip 80 of probe 10 may then be inserted into a sample and pump 20 operated to draw that sample through probe 10 and into the measuring chambers 14 and 16 of the sensing systems. Where desirable, probe 10 in its raised position may be further rotated, as required, to a position indicated by dotted lines in FIG. 5 and limited by the engagement of surfaces 126 and 136. Spring 98 acts to return probe 10 to its initial tilted position upon release of handle 84.

At the conclusion of sampling, solenoid 104 is actuated to move connector arm 102 downward and rotate latch plate 108 clockwise to release the holder 82. Spring 98 urges the holder downward and that holder is rotated into its initial vertical position by the engagement of surface 136 with the curved end surface 124 of the horizontal web 122 so that tip 80 is returned to alignment with the flush chamber 30. When probe 10 is in its lowered position, microswitch 96 is actuated to provide a signal indicating that the probe is in its lowered position, for example to interlock with other components of the system which are used in the flushing sequence.

Initially, reservoir 32 is filled with flush solution and connected to vent and syphon tubes 54, 56 as above described. The flush chamber 30 and intermediate chamber 34 are filled by closing the vent line and forcing flush solution through syphon tube 56, for example by compressing the flexible walls of reservoir 32, until the flush solution fills the intermediate chamber 34 to a level above the dam defined by port 38. Vent tube 54 is then opened and the liquid in the indicator chamber 40 and reservoir 32 stabilizes at a reduced pressure with flush solution rising in chamber 40 to the same level as that in reservoir 32. The reduced pressure above the flush solutions in the indicator chamber 40 and the reservoir 32 provides a stable system preventing the flush solution from overflowing intermediate chamber 34.

In this condition, after sampling, with probe 10 in its lowered position and immersed in flush solution, as indicated by interlock switch 96, pump 20 may be operated to draw flush solution through the measuring chambers 14, 16 in a cleaning sequence. Pump 20 draws solution from cup 30, that solution being replenished at a a slower rate through restricted opening 36. Accordingly, after an initial volume of flush solution is drawn into probe 10, the level of flush solution is drawn below tip 80 and air bubbles are entrained with the flush solution for flow with scrubbing action through the sample passage.

Replenishment of the flush solution in chamber 30 is through orifice 36 from intermediate chamber 34, that replenishment lowering the level of flush solution in chamber 34 until the peak 60 of port 38, as indicated in FIG. 3, is exposed to the atmosphere so that air passes through that port into the indicator chamber 40. The air bubble or bubbles rise into the vent space above the liquid in chamber 40 reducing the pressure in that vent space and thus permitting additional liquid to flow from reservoir 32 through syphon tube 56 to intermediate chamber 34 so that the liquid level in that chamber rises and closes port 58. Thus, as the cleaning sequence progresses with intermittent introduction of scrubbing air into the sample line, flush solution is periodically supplied to intermediate chamber 34 in an automatic replenishment action. This system effectively cleans the analysis system between analysis cycles in a simple and convenient manner, the probe being returned to flush position by energization of solenoid 104 and switch 96 signalling that probe position.

While a particular embodiment of the invention has been shown and described, various modifications thereof will be apparent to those skilled in the art and therefore it is not intended that the invention be limited to the disclosed embodiment or to details thereof, and departures may be made therefrom within the spirit and scope of the invention as defined by the claims.

What is claimed is:

1. In an analysis system of the type that has an elongated sample passage open at one end to define a sample entrance and a sensor communicating with said sample passage for sensing a constituent of a sample in said sample passage, cleaning apparatus comprising a reservoir for cleaning liquid, a flush chamber having an open upper end and a restricted opening in communication with said reservoir for replenishing cleaning liquid in said flush chamber as used, support means for guiding the movement of said sample entrance between a first position with said sample entrance in said flush chamber and a second position with said sample entrance removed from said flush chamber for receiving a liquid sample, and a pump for drawing cleaning liquid from said flush chamber through said sample passage more rapidly than said flush chamber may be replenished with cleaning liquid from said reservoir by flow through said restricted opening, thereby causing, after an initial continuous flow of cleaning liquid through said sample entrance, the entrainment of air bubbles in the cleaning liquid entering said sample entrance for flow through said sample passage, said entrained air bubbles producing a scrubbing action as said cleaning liquid flows through said sample passage.

2. The apparatus as claimed in claim 1 and further including an intermediate chamber having an upper end above the position of said sample entrance in said first position and open to the atmosphere, and wherein said flush chamber is a flush cup that has a downwardly extending tubular portion with said restricted opening at the bottom of said tubular portion, said flush cup being removably supported in said intermediate chamber with said restricted opening adjacent but spaced above the bottom of said intermediate chamber and said intermediate chamber extending above.

3. The apparatus as claimed in claim 2 wherein said reservoir has a closed upper end disposed above the upper end of said intermediate chamber, a control aperture in the wall of said intermediate chamber above the position of said sample entrance in said first position and a tube providing communication between said control opening and the upper end of said reservoir, said control opening having upper side walls that slope outwardly away from a peak and said peak extending outwardly in an upwardly inclined direction from the inner surface of said intermediate chamber, operation of said pump drawing liquid from said flush cup and being replenished by flow through said restricted opening to lower the level of liquid in said intermediate chamber and expose the peak of said control opening to the atmosphere so that air passes through said control opening and said tube into the closed upper end of said reservoir and allowing additional cleaning liquid to flow from said reservoir to said intermediate chamber to raise the liquid level in said intermediate chamber and close said control opening.

4. The apparatus as claimed in claim 1 in which said flush chamber opening is of smaller area than said sample entrance whereby said pump may be operated to draw cleaning liquid through said sample passage more rapidly than said flush chamber may be replenished with cleaning liquid from said reservoir thereby causing air bubbles to enter said passage after an initial continuous flow of cleaning liquid.

5. The apparatus as claimed in claim 4 in which said vent opening comprises a tube and said reservoir and said vent tube have flexible walls.

6. In an analysis system of the type that has an elongated sample passage open at one end to define a sample entrance, a sensor communicating with said sample passage for sensing a constituent of said sample and a pump connected with said sample passage for moving fluid through said passage, apparatus comprising a reservoir for cleaning liquid, a flush chamber having an open upper end and a lower portion in communication with said reservoir for replenishing cleaning liquid in said flush chamber as used, a guideway above said flush chamber, a holder connected to said guideway for movement toward and away from said flush chamber, said sample entrance being connected to said holder for movement therewith between a first position with said sample entrance extended into said flush chamber and a second position with said sample entrance removed from said flush chamber for receiving a liquid sample, a biasing member for urging said holder toward said first position, a latch for releasably maintaining said sample entrance in said second position, and a latch release mechanism, whereby in said first position said sample entrance may be immersed in cleaning liquid and said pump may be operated to draw cleaning liquid through said passage.

7. The apparatus as claimed in claim 6 and further including a sensor for providing a signal when said sample entrance is in said first position.

8. Liquid feeding apparatus comprising:
a first chamber having an open top;
a reservoir vertically extending to a position spaced above the top of said first chamber;
a liquid feed opening between said reservoir and said first chamber; and
a flush cup extending downwardly into said first chamber and having a restricted opening at the bottom thereof spaced above and adjacent the bottom of said first chamber.

9. The apparatus as claimed in claim 8 wherein said reservoir is closed and further including a control opening between said reservoir and said first chamber, said control opening being exposed to the atmosphere as the liquid level in said first chamber is drawn down to allow flow of liquid from said reservoir through said feed opening to said first chamber.

10. The apparatus as claimed in claim 9 wherein said feed opening and said control opening are contiguous.

11. Liquid feeding apparatus comprising:
a first chamber having an open top;
a reservoir vertically extending to a position spaced above the top of said first chamber and having a closed top;
a liquid feed opening and a control opening between said reservoir and said first chamber, said control opening being exposed to the atmosphere as the liquid level in said first chamber is drawn down to allow flow of liquid from said reservoir through said feed opening to said first chamber; and
a flush cup supported at the top of said first chamber, said cup extending downwardly into said first chamber and having a restricted opening at the bottom thereof spaced above and adjacent the bottom of said first chamber.

12. The apparatus as claimed in claim 11 and further including a liquid level indicator chamber having a closed upper end and having a height, extending above the top of said first chamber, said control opening communicating said indicator chamber with said first chamber adjacent and below the upper end of said first chamber, wall means preventing communication thereabove, said apparatus further including a vent opening communicating the upper ends of said indicator chamber and said reservoir.

13. The apparatus as claimed in claim 12 and further including a syphon tube extending from adjacent the lower portion of said reservoir, through the top thereof and thence to said first chamber.

14. The apparatus as claimed in claim 13 in which said restricted opening is of smaller area than the sample entrance of a probe to be cleaned whereby a pump may be operated to draw cleaning liquid through said sample entrance more rapidly than said flush cup may be replenished with cleaning liquid from said reservoir thereby causing air bubbles entrained in cleaning liquid to enter said sample entrance after an initial continuous flow of cleaning liquid.

15. Probe mounting and positioning apparatus comprising
a holder to which said probe is secured;
guide structure in said holder;
a guide housing having a guide channel therein, said guide structure extending into said guide channel, said guide channel together with said guide structure defining raised and lowered probe positions;
a biasing member secured to said holder;
a latch adjacent the upper end of said guide channel adapted to releasably secure said holder in said raised probe position; and
means for releasing said latch to allow said biasing member to move said holder toward said lowered probe position.

16. The apparatus claimed in claim 15 in which latch comprises a latch plate pivotally connected to said guide housing below the upper end of said guide channel and having a latch surface at the upper end of said guide channel for engaging said holder to hold said holder in said raised probe position.

17. The apparatus claimed in claim 15 in which said means for releasing said latch comprises a solenoid connected to said latch plate.

18. The apparatus as claimed in claim 15 and further including a sensor for providing a signal when said probe is in said lowered position.

19. The apparatus as claimed in claim 15 and further including structure permitting rotational movement of said probe when said probe is secured in said raised probe position to change the location of the entrance of said probe.

20. The apparatus as claimed in claim 15 and further including cleaning liquid feeding apparatus comprising:
a first chamber having an open top;
a reservoir vertically extending to a position spaced above the top of said first chamber;
a cleaning liquid feed opening between said reservoir and said first chamber; and
a flush chamber having a restricted opening in communication with said first chamber, the entrance of said probe being disposed in said flush chamber in said lowered probe position.

21. The apparatus as claimed in claim 20 wherein said flush chamber is a flush cup positioned at the top of said first chamber, said cup extending downwardly into said first chamber and having said restricted opening at the bottom thereof spaced above and adjacent the bottom of said first chamber.

22. The apparatus as claimed in claim 21 wherein said reservoir is closed and further including a control opening between said reservoir and said first chamber, said control opening being exposed to the atmosphere as the liquid level in said first chamber is drawn down to allow flow of liquid from said reservoir through said feed opening to said first chamber.

23. The apparatus as claimed in claim 22 and further including a liquid level indicator chamber having a closed upper end and having a height, extending above the top of said first chamber, said control opening communicating said indicator chamber with said first chamber adjacent and below the upper end of said first chamber, wall means preventing communication thereabove, said flush system further including a vent opening communicating the upper ends of said indicator chamber and said reservoir, and further including a syphon tube extending from adjacent the lower portion of said reservoir, through the top thereof and thence to said first chamber.

24. The apparatus as claimed in claim 23 in which said restricted opening is of smaller area than the sample entrance of a probe to be cleaned whereby a pump may be operated to draw cleaning liquid through said sample entrance more rapidly than said flush chamber may be replenished with cleaning liquid from said reservoir thereby causing air bubbles to enter said sample entrance after an initial continuous flow of cleaning liquid.

* * * * *